United States Patent [19]

Urich

[11] Patent Number: 5,476,448

[45] Date of Patent: Dec. 19, 1995

[54] APPARATUS FOR SUPPRESSING A VACUUM SURGE IN EYE SURGERY

[76] Inventor: Alex Urich, 27402 Via Caudaloso, Mission Viejo, Calif. 92692

[21] Appl. No.: 325,680

[22] Filed: Oct. 19, 1994

[51] Int. Cl.⁶ ............................................. A61B 17/20
[52] U.S. Cl. ........................ 604/22; 604/22; 604/31; 606/167; 137/207; 138/30
[58] Field of Search ........................... 604/22, 27, 30, 604/34, 35, 118, 119, 131, 133, 140, 141, 245, 246, 247, 289, 294, 298, 319; 606/107, 161; 138/30, 26; 137/123, 207, 888; 417/540

[56] References Cited

U.S. PATENT DOCUMENTS

| | | | |
|---|---|---|---|
| 2,886,053 | 5/1959 | Wilson | 137/207 |
| 3,882,872 | 5/1975 | Douvas et al. | 128/305 |
| 3,902,495 | 9/1975 | Weiss et al. | 128/276 |
| 4,364,416 | 12/1982 | Jacobellis et al. | 138/30 |
| 5,058,570 | 10/1991 | Idemoto et al. | 128/24 AA |
| 5,322,504 | 6/1994 | Doherty et al. | 606/167 |
| 5,399,160 | 3/1995 | Dunberger et al. | 604/31 |
| 5,413,556 | 5/1995 | Whittingham | 604/22 |

*Primary Examiner*—C. Fred Rosenbaum
*Assistant Examiner*—Laird J. Knights
*Attorney, Agent, or Firm*—Blakely, Sokoloff, Taylor & Zafman

[57] ABSTRACT

A surge suppresser which has a collapsible flexible wall that accumulates the aspiration fluid of an interocular surgical system. The surge suppresser has an inlet port and an outlet port that are connected to an aspiration line downstream from a surgical tip. The aspiration line is connected to a vacuum device which draws fluid from the tip. When an occlusion in the aspiration line occurs, the decrease in pressure caused by the vacuum device will cause the flexible wall to collapse and close the inlet and outlet ports of the surge suppresser. When the occlusion breaks, the inlet port initially opens and the outlet port remains closed so that the flexible wall is expanded by the flow of fluid from the surgical tip. The closed outlet port prevents a surge of fluid from the eye. Additionally, the ports are arranged in a parallel relationship to reduce the momentum of the fluid into the suppresser and further limit the surge of fluid from the eye. As the flexible wall gradually expands, the outlet port opens and allows the fluid to flow through the suppresser.

11 Claims, 1 Drawing Sheet

APPARATUS FOR SUPPRESSING A VACUUM SURGE IN EYE SURGERY

BACKGROUND OF THE INVENTION

1. Field of the Invention

The present invention relates to a vacuum surge protector for the aspiration line of an interocular surgical system.

2. Description of Related Art

Human tissue is sometimes emulsified with an ultrasonic instrument. For example, cataracteous lenses are typically removed with an ultrasonic tip that is inserted into the cornea of the patient. The vibrating tip emulsifies the lens into small particles that are removed by an irrigation/aspiration system coupled to the ultrasonic instrument. A conventional interocular fluid system includes an irrigation line that is connected to a gravity bottle which supplies an irrigation fluid to the tip of the instrument. The fluid system also contains an aspiration line that is attached to an inner channel of the ultrasonic tip. The aspiration line is typically connected to a vacuum pump which draws the fluid and lens particles away from the surgical site.

Some of the lens particles may become occluded within the aspiration line and interrupt the flow of fluid from the eye. An occlusion of the aspiration line will create an increase in the vacuum pressure downstream from the point of blockage. Likewise, the gravity bottle will create an increase in the fluid pressure upstream from the occlusion. The pressure differential across the aspiration line will cause a corresponding surge in the flow of fluid from the eye if the occlusion becomes dislodged. The pressure surge can cause the cornea to collapse and damage the eye.

U.S. Pat. Nos. 5,106,367 and 5,167,620 issued to Ureche et al. disclose a surge suppresser for an interocular surgical system. The Ureche surge suppresser is a tube which has a wall that is thinner than the wall of the aspiration line. When an occlusion occurs, the tube wall collapses and increases the fluid resistance within the aspiration line. When the occlusion dislodges, the collapsed wall prevents any sudden surge in the flow of fluid from the eye. Although effective in preventing vacuum surges in the system, the Ureche tube is susceptible to occlusions within the tube itself.

SUMMARY OF THE INVENTION

The present invention is a surge suppresser which has a collapsible flexible wall that accumulates the aspiration fluid of an interocular surgical system. The surge suppresser has an inlet port and an outlet port that are connected to an aspiration line downstream from a surgical tip. The aspiration line is connected to a vacuum device which draws fluid from the tip. When an occlusion in the aspiration line occults, the decrease in pressure caused by the vacuum device will cause the flexible wall to collapse and close the inlet and outlet ports of the surge suppresser. When the occlusion breaks, the inlet port initially opens and the outlet port remains closed so that the flexible wall is expanded by the flow of fluid from the surgical tip. The closed outlet port prevents a surge of fluid from the eye. Additionally, the ports are arranged in a parallel relationship to reduce the momentum of the fluid into the suppresser and further limit the surge of fluid from the eye. As the flexible wall gradually expands, the outlet port opens and allows the fluid to flow through the suppresser.

BRIEF DESCRIPTION OF THE DRAWINGS

The objects and advantages of the present invention will become more readily apparent to those ordinarily skilled in the art after reviewing the following detailed description and accompanying drawings, wherein.

DETAILED DESCRIPTION OF THE INVENTION

Figure 1:
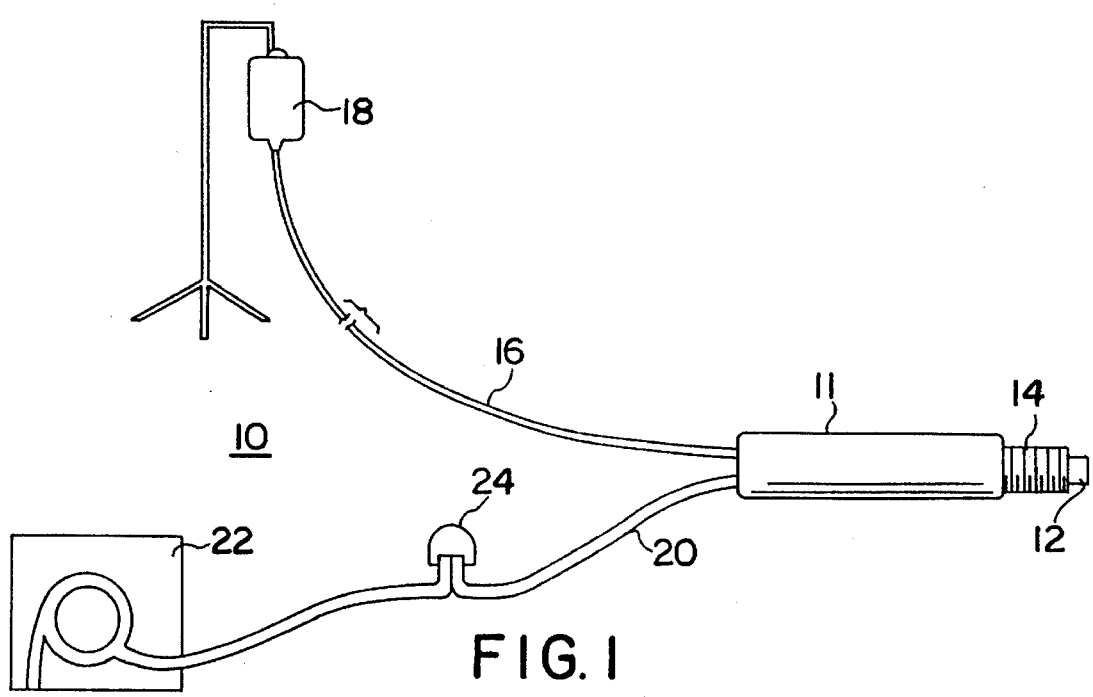
FIG. 1 is a schematic of an interocular surgical system with a surge suppresser of the present invention.

Referring to the drawings more particular by reference numbers, FIG. 1 shows an interocular surgical system 10 of the present invention. The system 10 may include a surgical instrument 11 which has an ultrasonically driven tip 12 that is inserted into a cornea. The vibrating tip 12 can emulsify tissue into a plurality of small particles. The tip 12 is partially covered with a sleeve 14. The sleeve 14 and tip 12 form an inner channel (not shown) that is connected to an irrigation line 16. The irrigation line 16 is typically connected to a gravity bottle 18 filled with an irrigation fluid. The gravity bottle 18 provides pressurized fluid to the surgical site to cool and irrigate the eye. The tip 12 may have an inner channel (not shown) that is connected to an aspiration line 20. The aspiration line 20 is connected to a vacuum pump 22 which draws fluid from the surgical site. Located within the aspiration line 20 is a surge suppresser 24. Although an interocular instrument is shown and described, it is to be understood that the surge suppresser 24 of the present invention can be used in other surgical aspiration systems.

Figure 2:
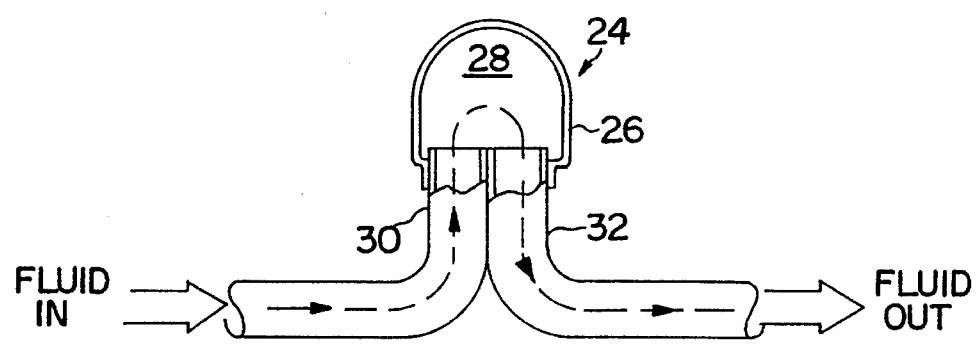
FIG. 2 is a cross-sectional view of the surge suppresser.

As shown in FIG. 2, the surge suppresser 24 has a collapsible flexible wall 26 that defines an accumulator chamber 28. The suppresser 24 also has an inlet port 30 and an outlet port 32 that provide fluid communication between the aspiration line 20 and the accumulator chamber 28. The inlet 30 and outlet 32 ports are typically tubes that can be readily attached to the aspiration line 20. The wall 26 must be flexible enough and large enough to close both ports 30 and 32 when in a collapsed position. In the preferred embodiment, the flexible wall 26 is constructed from a silicone that is 0.001–0.002 inches thick. Additionally, the inlet 30 and outlet 32 ports are preferably larger than the aspiration line 20 to prevent any occlusion of the surge suppresser 24. In the preferred embodiment, the ports have a diameter between 0.02–0.2 inches and a tube length of 0.25–5.0 inches.

The ports 30 and 32 are adjacent and parallel to each other so that the velocity vector of the fluid flowing into the chamber 28 from the inlet port 30 is 180° from the velocity vector of the fluid flowing through the outlet port 32. The parallel ports reduce the momentum of the fluid and limit a flow surge through the aspiration line 20. The reduction in fluid momentum also cause the particles to collect within the accumulator chamber 28. It is preferable to construct the flexible wall 26 from a transparent material so that the surgeon can see the accumulation of particles within the chamber to verify that the ultrasonic tip 12 is emulsifying tissue. The reduction in fluid momentum also reduces the probability of the particles combining to form an occlusion within the ports of the surge suppresser 24.

Figure 3:
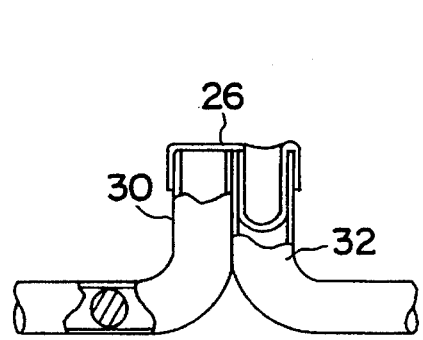
FIG. 3 is a cross-sectional view showing the surge suppresser in a collapsed condition.
Figure 4:
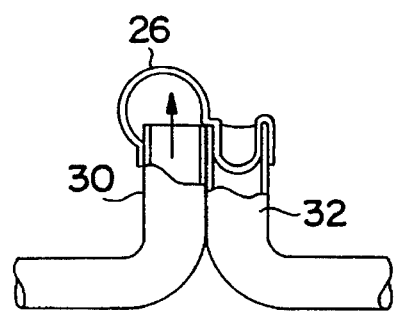
FIG. 4 is a cross-sectional view showing the surge suppresser with an inlet port open and an outlet port closed.

As shown in FIG. 3, when an occlusion 34 occurs, the vacuum pump 22 will decrease the pressure downstream from the occlusion and the gravity bottle 18 will increase the fluid pressure upstream from the occlusion. The decrease in pressure will cause the flexible wall 26 to collapse and close the inlet port 30 and the outlet port 32 of the surge suppresser. As shown in FIG. 4, when the occlusion becomes dislodged from the aspiration line, the high pressure of the fluid upstream from the surge suppresser will open the inlet port 30 and the vacuum downstream from the surge suppresser will maintain the outlet port 32 in the closed position. Fluid will flow into the accumulator chamber 28 and expand the flexible wall 26. The expansion of the flexible wall 26 and the accumulation of aspiration fluid prevents a sharp surge in the flow of fluid from the eye. The expansion of the wall 26 will eventually open the outlet port 32 and allow fluid to flow through the suppresser 24. The change of fluid momentum through the suppresser prevents a sudden surge in fluid flow when the outlet port 32 is opened and the vacuum pressure is introduced to the system.

The accumulator chamber 28 is preferably larger than the fluid volume of the anterior chamber of a cornea. The relatively large accumulator volume provides a fluid capacitor that absorbs the energy of a vacuum surge, particularly if the occlusion is downstream from the surge suppresser. In the preferred embodiment, the volume of the accumulator is 0.2–2.0 cubic centimeters. The accumulator chamber 28 can also provide a reservoir of fluid which can be forced through the aspiration line 20 and tip 12 by squeezing the flexible wall 26. Squeezing the flexible wall 26 allows the surgeon to dislodge occlusions within the system.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A surge suppresser for an aspiration line of a surgical instrument, comprising:

an accumulator that has a collapsible flexible wall, an inlet port and an outlet port, said flexible wall closes said inlet port and said outlet port when in a collapsed condition, said flexible wall having a shape and flexibility that allows said inlet port to open before said outlet port is opened when said collapsed accumulator is filed with fluid through said inlet port.

2. The surge suppresser as recited in claim 1, wherein said flexible wall is constructed from silicone that is no greater than 0.002 inches thick.

3. The surge suppresser as recited in claim 1, wherein said inlet port and said outlet port are adjacent and parallel.

4. The surge suppresser as recited in claim 1, wherein said flexible wall is transparent.

5. A surgical aspiration system for supplying and removing a fluid from a surgical site and for damping a pressure spike created by an occlusion in the system, comprising:

a supply line for supplying a fluid to the surgical site;

an aspiration line for removing the fluid from the surgical site;

a vacuum device connected to said aspiration line; and, an accumulator that has an inlet port in fluid communication with the surgical site, an outlet port in fluid communication with said vacuum device, and a collapsible flexible wall, said flexible wall collapses and closes said outlet port when the occlusion reduces a pressure in said aspiration line.

6. The system as recited in claim 5, wherein said flexible wall closes said inlet port and said outlet port when in a collapsed condition.

7. The system as recited in claim 5, wherein said flexible wall is constructed from silicone that is no greater than 0.002 inches thick.

8. The system as recited in claim 5, wherein said inlet port and said outlet port are adjacent and parallel.

9. The system as recited in claim 5, wherein said flexible wall is transparent.

10. The system as recited in claim 5, further comprising a surgical ultrasonic tip that is coupled to said supply line and said aspiration line and which is inserted into a cornea.

11. The system as recited in claim 5, wherein said flexible wall has a shape and a flexibility that opens said inlet port before said outlet port when said collapsed accumulator is filled with fluid through said inlet port.

* * * * *